United States Patent [19]

Matsumura et al.

[11] 4,269,838

[45] May 26, 1981

[54] CARBAMYL PIPERAZINE DERIVATIVES

[75] Inventors: Shingo Matsumura, Kyoto; Hiroshi Enomoto, Nagaokakyo; Yoshiaki Aoyagi, Kyoto; Haruo Tanaka, Hikone, all of Japan

[73] Assignee: Nippon Shinyaku Co. Ltd., Japan

[21] Appl. No.: 87,363

[22] Filed: Oct. 23, 1979

[30] Foreign Application Priority Data

Oct. 23, 1978 [JP] Japan ................. 53-130922

[51] Int. Cl.$^3$ ................. C07D 295/20; C07D 31/495
[52] U.S. Cl. ..................................... 424/250; 544/390
[58] Field of Search ........................ 544/390; 424/250

[56] References Cited

U.S. PATENT DOCUMENTS 3,919,233  11/1975  Rebling ................. 544/390

Primary Examiner—Mark L. Berch
Attorney, Agent, or Firm—Jacobs & Jacobs

[57] ABSTRACT 4-(3-Aryloxy-2-hydroxypropyl)piperazines bearing a carbamyl, N-alkyl or N,N-dialkylcarbamyl group in the 1-position are β-adrenergic blockers. A typical example is 1-carbamyl-4-(3-phenoxy-2-hydroxypropyl)piperazine.

46 Claims, No Drawings

CARBAMYL PIPERAZINE DERIVATIVES

DETAILED DESCRIPTION

This invention relates to 1-carbamylpiperazine derivatives substituted in the 4-position by a 3-aryloxypropan-2-ol substituent.

It is well known that the β-action of adrenalin is antagonized by various derivatives of phenoxypropanolamine and considerable study has been devoted to structure-activity correlations, particularly with regard to the organ selectivity arising from different substituents on the aromatic ring and different substituents on the amine. It has been considered essential for β-blockers of this type that the amine should be secondary; i.e., monosubstituted. Thus the amine substituent of known phenoxypropanol-type β-blockers almost without exception are secondary, isopropylamino and tert-butylamino being present in most of conventional structures. Tertiary amino structures appear to produce only very low activity. See, e.g. E. J. Ariëns, Ed.; Drug Design, Vol. III, p 205, Academic Press, New York, 1972. See also, for example, U.S. Pat. Nos. 3,410,901, 3,432,545, 3,637,852, 3,872,147, 3,857,873, and 4,045,482. The compounds of this invention are piperazine derivatives and, therefore, analogous to tertiary-amino type. More significantly, these compounds have a carbamyl group in the 4-position of the piperazine ring. These structural features have never been seen in the prior art compounds having β-adrenergic blocking activity. Surprisingly, compounds corresponding to the compounds of this invention but which lack the carbamyl group do not exhibit β-blocking activity at all. The blocking activity of the compounds according to this invention is extremely high, superior in fact to the activity of known β-blocker compounds.

The compounds according to this invention can be represented by the following structural formula:

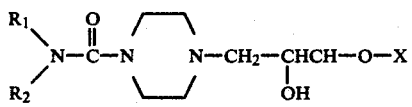

wherein each of $R_1$ and $R_2$, independently of the other, is hydrogen or lower alkyl, and X is naphthyl or

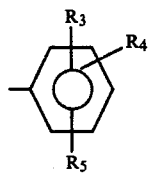

wherein each of $R_3$, $R_4$ and $R_5$, independently of the others, is selected from the group consisting of hydrogen, hydroxy, halo, lower alkyl, lower alkoxy, lower alkanamido and benzyloxy.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

The term halo denotes the monovalent substituents fluoro, chloro, bromo and iodo.

The compounds of the present invention can exist as optical isomers and both the racemates of these isomers and the individual isomers themselves are within the scope of the present invention. The racemates can be separated into their individual isomers through the well known technique such as forming diastereoisomeric salts.

The compounds of this invention interfer with the transmission of postganglionic impulses by blockage of the sympathetic receptor. Blockage of the β-receptor decreases inotropic, chronotropic and metabolic effects on the heart and in some cases can stop arrhythmias produced by excess epinephrine. Angina can in some instances be prevented as a result of the decreased need for oxygen by the heart.

β-receptor blockers are characterized by their antagonism to isoproterenol (N-isopropyl-nor-adrenaline) and practical use of these compounds are those clinical conditions such as hypertension, angina, arrhythmias and the like where β-receptor blocking or isoproterenol antagonism is indicated.

In view of the nature of the indications, the dose administered must be carefully titrated to the patient, utilizing sound professional judgment and taking into consideration the age, weight and condition of the patient and the desired response. Generally a response will be observed for a patient of average weight (e.g. about 70 kg) at an oral dose of 5 to 30 mg 3 to 4 times a day. A typical parenteral dose (i.v.) is from 1 to 5 mg for a patient of average weight slowly administered.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The compounds can be prepared by a number of methods previously utilized for other compounds of this type. The most general route comprises the reaction of a phenylglycidyl ether with piperazine and N-carbamylation of the reaction product. The carbamylation reaction is conducted conventionally with a cyanate or nitrourea. For N-alkylcarbamylation, a reactive carbamylating agent such as N-alkylcarbamyl chloride or an alkyl isocyanate can be employed with advantage. Alternatively, one can prepare the N-carbamylpiperazine and then allow the same to react with the phenylglycidyl ether.

The synthesis of some representative compounds is described in the following examples.

EXAMPLE 1

1-Carbamyl-4-[3-(4-chlorophenoxy)-2-hydroxypropyl]-piperazine (HCl)

A. While 9.3 g of piperazine is refluxed in 50 ml of methanol with stirring, 10 g of p-chlorophenyl glycidyl ether are added dropwise over a period of 1.5 hours. After the addition has been completed, the mixture is refluxed with stirring for a further 1.5 hours, and then concentrated to dryness under reduced pressure. The residue is dissolved in dilute hydrochloric acid and extracted with ethyl acetate. The water layer is rendered basic with sodium hydroxide, extracted first with benzene from which there can be obtained N,N'-bis[3-(4-chlorophenoxy)-2-hydroxypropyl]piperazine, and then with n-butanol. The butanol extracts are washed with water and the solvent then removed by distillation under reduced pressure to yield 10.0 g of N-[3-(4-chlorophenoxy)-2-hydroxypropyl]piperazine as a colorless oil.

B. To a mixture of 5.0 g of this piperazine in 20 ml of methanol is added 1.94 g of nitrourea. The mixture is heated under reflux for 2 hours. The methanol is removed by distillation and the residue is dissolved in ethanolic hydrogen chloride with heating and then allowed to stand. The title compound is obtained as crystals which are recrystallized from ethanol. Yield: 3.34 g; m.p. 193°–196° C.

EXAMPLE 2

1-Carbamyl-4-[3-(4-methoxyphenoxy)-2-hydroxypropyl]piperazine (HCl)

Following the procedure of part A of Example 1, 9.56 g of piperazine is allowed to react with 10 g of p-methoxyphenyl glycidyl ether to obtain 7.5 g of N-[3-(4-methoxyphenoxy)-2-hydroxypropyl]-piperazine.

Three (3.0) g of the product and 1.18 g of nitrourea in 20 ml of methanol are heated at reflux with stirring for 4 hours. The solvent is removed by distillation, the residue dissolved in ethanol and hydrogen chloride gas bubbled through the solution. The title compound is obtained as crystals which are recrystallized from isopropyl alcohol. Yield: 1.44 g; m.p. 192°–195° C.

EXAMPLE 3

1-Carbamyl-4-[3-(4-benzyloxyphenoxy)-2-hydroxypropyl]piperazine

In the same manner as described in Example 1A, 13.1 g of piperazine is allowed to react with 20 g of p-benzyloxyphenyl glycidyl ether to obtain 16 g of the monosubstituted piperazine intermediate. This compound is then allowed to react with 5.4 g of nitrourea in 50 ml of methanol under reflux with stirring for 3 hours as described in Example 1B, after which the methanol is removed by distillation under reduced pressure. The residue is dissolved in methanol, hydrogen chloride is introduced and the title compound as the hydrochloride is obtained as crystals which are recrystallized from isopropyl alcohol. Yield: 12.9 g; m.p. 201°–204° C.

EXAMPLE 4

1-Carbamyl-4-[3-(2,3-dimethoxyphenoxy)-2-hydroxypropyl]piperazine

In the same manner as described in Example 1A, 6.6 g of piperazine is allowed to react with 8.1 g of 2,3-dimethoxyphenyl glycidyl ether and the reaction mixture treated to obtain 5.3 g of the intermediate. Following the procedure of Example 1B, a solution of 5.2 g of this product in 150 ml of methanol and 2.28 g of nitrourea is heated at reflux for one hour. The reaction mixture is concentrated to dryness under reduced pressure, the residue dissolved in ethanol and hydrogen chloride is bubbled through the solution. The resulting solid is collected to yield the title compound as the hydrochloride which is recrystallized from ethanol. Yield: 4.48 g; m.p. 171°–174° C.

EXAMPLE 5

1-Carbamyl-4-[3-(2,4-dichlorophenoxy)-2-hydroxypropyl]piperazine

In the same manner as described in Example 1A, 7.0 g of piperazine is reacted with 7.4 g of 2,4-dichlorophenyl glycidyl ether and the reaction mixture treated as therein described to produce 6.9 g of the piperazinophenoxypropanol intermediate. In 50 ml of acetic acid are dissolved 3.4 g of this compound and, after addition of 2.0 g of potassium cyanate, the solution is stirred to 50° to 55° C. for 8 hours. The reaction mixture is concentrated to dryness under reduced pressure, water is added to the residue and the mixture rendered basic with ammonia and extracted with n-butanol. The n-butanol extracts are purified by silica gel column chromatography with a 4:1 chloroform:methanol to yield the product which is then converted to the hydrochloride and recrystallized from ethanol. Yield: 1.81 g; m.p. 198°–201° C.

EXAMPLE 6

1-Methylcarbamyl-4-(3-phenoxy-2-hydroxypropyl)piperazine

In the same manner as Example 1A, 9.3 g of piperazine is allowed to react with 10 g of phenyl glycidyl ether and the reaction mixture worked up as therein described to yield 10.9 g of the monosubstituted intermediate.

In 20 ml of benzene are dissolved 3.0 g of this intermediate and to the resulting solution are added 600 mg of methyl isocyanate. The mixture is stirred at room temperature for 2 hours. The benzene is then removed by distillation under reduced pressure to yield the product as crystalline residue which is recrystallized from isopropyl alcohol. Yield: 1.59 g; m.p. 91°–95° C.

EXAMPLE 7

1-Dimethyl carbamyl-4-(3-phenoxy-2-hydroxypropyl)piperazine

In 20 ml of benzene are dissolved 5.0 g of the N-(3-phenoxy-2-hydroxypropyl)piperazine intermediate (described in Example 6) and 2.3 g of triethylamine. To this solution are then added dropwise, with stirring and at room temperature, 2.5 g of N,N-dimethylcarbamyl chloride over a period of 30 minutes. When the addition is complete, the mixture is stirred for a further 4 hours, at the end of which time the benzene solution is washed with water and dried. The benzene is removed by distillation and the residue purified by silica gel column chromatography, eluting with 4:1 chloroform:methanol to yield the product as a colorless oil which crystallizes only with difficulty. NMR spectrum (TMS as internal reference, δ) 2.73 (CCl$_4$), 2.80 (CD$_3$OD) (dimethylamino group). Yield: 1.5 g; IR spectrum: $v_{max}^{film}$ 1625 cm$^{-1}$ (carbonyl).

EXAMPLE 8

1-Diethylcarbamyl-4-[3-(naphth-1-yloxy)-2-hydroxypropyl]piperazine

In the same manner as described in Example 1A, 9.1 g of piperazine is allowed to react with 10.8 g of α-naphthyl glycidyl ether to yield 10.0 g of N-[3-(naphth-1-yloxy)-2-hydroxypropyl]-piperazine. Five grams of this compound and 2.3 g of triethylamine are dissolved in 20 ml of benzene and, with stirring and at room temperature, 3.16 g of N,N-diethylcarbamyl chloride are added dropwise over a period of 30 minutes. When the addition is complete, the mixture is heated at reflux for 2 hours and, after cooling, washed with water and dried. The solvent is removed by distillation, the residue dissolved in ethanol and hydrogen chloride bubbled through the solution. The title compound is thus obtained as the hydrochloride which is recrystallized from isopropyl alcohol. Yield: 2.44 g; m.p. 152°–156° C.

EXAMPLE 9

1-Carbamyl-4-[3-(4-hydroxyphenoxy)-2-hydroxypropyl]piperazine

Eight grams of the product obtained in Example 3 are dissolved in a mixture of 50 ml methanol and 30 ml water, 500 mg of 5% palladium-on-carbon are added, and catalytic reduction is carried out until the uptake of hydrogen has ceased (about 18 hours). The catalyst is removed by filtration, the filtrate is concentrated to dryness under reduced pressure and the crystalline residue constituting the product is recrystallized from isopropyl alcohol. Yield: 2.72 g; m.p. 198°–201° C.

Additional embodiments of the invention prepared in analogous fashion are presented in the following table, compounds 2, 9, 13, 19, 23, 24, 28, 31 and 12 corresponding to the products of Example 1–9, respectively.

TABLE

| Compound No. | $R_1$ | $R_2$ | X | m.p. (°C.) |
|---|---|---|---|---|
| 1 | H | H | —⟨O⟩ | Hydrochloride 189–191 |
| 2 | " | " | —⟨O⟩—Cl | Hydrochloride 193–196 |
| 3 | " | " | —⟨O⟩ (Br) | Hydrochloride 196–199 |
| 4 | " | " | F—⟨O⟩ | Hydrochloride 189–191 |
| 5 | " | " | —⟨O⟩—CH$_3$ | Hydrochloride 197–200 |
| 6 | " | " | CH$_3$—⟨O⟩ | Hydrochloride 200–203 |
| 7 | " | " | —⟨O⟩ (C$_2$H$_5$) | Hydrochloride 198–201 |
| 8 | " | " | —⟨O⟩—C(CH$_3$)$_3$ | Hydrochloride 237–242 |
| 9 | " | " | —⟨O⟩—OCH$_3$ | Hydrochloride 192–195 |
| 10 | " | " | —⟨O⟩ (OCH$_3$) | Hydrochloride 187–190 |
| 11 | " | " | CH$_3$O—⟨O⟩ | Hydrochloride 191–194 |
| 12 | " | " | —⟨O⟩—OH | Hydrochloride 198–201 |
| 13 | " | " | —⟨O⟩—O—CH$_2$—⟨O⟩ | Hydrochloride 201–204 |
| 14 | " | " | —⟨O⟩—NHCOCH$_3$ | Hydrochloride 147–150 |

TABLE-continued

| Compound No. | R₁ | R₂ | X | m.p. (°C.) |
|---|---|---|---|---|
| 15 | " | " | naphthyl | Hydrochloride 227–230 |
| 16 | " | " | naphthyl | Hydrochloride 205–208 |
| 17 | " | " | phenyl-OCH₃, OCH₃ | Hydrochloride 187–189 |
| 18 | " | " | CH₃O-phenyl-OCH₃ | Hydrochloride 174–176 |
| 19 | " | " | phenyl with CH₃O, OCH₃ | Hydrochloride 171–174 |
| 20 | " | " | phenyl-OCH₃ with CH₃O, OCH₃ | Hydrochloride 166–169 |
| 21 | " | " | phenyl-CH₃, Cl | Hydrochloride 207–210 |
| 22 | " | " | Cl-phenyl-OCH₃ | Hydrochloride 203–205 |
| 23 | " | " | Cl-phenyl-Cl | Hydrochloride 198–201 |
| 24 | " | CH₃ | phenyl | 91–95 |
| 25 | " | " | naphthyl | Hydrochloride 205–208 |
| 26 | " | C₂H₅ | phenyl | p-Tosylate 170–175 |
| 27 | " | " | naphthyl | Hydrochloride 210–215 |
| 28 | CH₃ | CH₃ | phenyl | Oil |
| 29 | " | " | naphthyl | Hydrochloride 136–140 |
| 30 | C₂H₅ | C₂H₅ | phenyl | Hydrochloride 132–134 |
| 31 | " | " | naphthyl | Hydrochloride 152–156 |

What is claimed is:

1. A compound selected from the group consisting of a carbamylpiperazine of the formula:

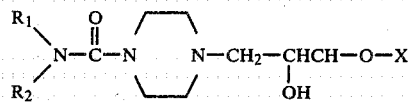

and the pharmaceutically acceptable acid addition salts thereof wherein each of $R_1$ and $R_2$, independently of the other, is hydrogen or lower alkyl, and X is naphthyl or

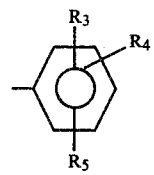

wherein each of $R_3$, $R_4$ and $R_5$, independently of the others, is selected from the group consisting of hydrogen, hydroxy, halo, lower alkyl, lower alkoxy, lower alkanamido and benzyloxy.

2. A compound according to claim 1 wherein each of $R_1$ and $R_2$ is hydrogen.

3. A compound according to claim 2 wherein X is naphthyl.

4. A compound according to claim 2 wherein X is

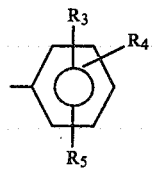

in which $R_3$, $R_4$ and $R_5$ are as therein defined.

5. A compound according to claim 2 wherein each of $R_3$, $R_4$ and $R_5$, independently of the others, is selected from the group consisting of hydrogen, bromo, chloro, fluoro, methyl, ethyl, methoxy, acetamido and benzyloxy.

6. A compound according to claim 1 wherein $R_1$ is hydrogen and $R_2$ is lower alkyl of 1 to 4 carbon atoms.

7. A compound according to claim 1 wherein X is naphthyl.

8. A compound according to claim 6 wherein each of $R_3$, $R_4$ and $R_5$, independently of the others, is selected from the group consisting of hydrogen, bromo, chloro, fluoro, methyl, ethyl, methoxy, acetamido and benzyloxy.

9. A compound according to claim 8 wherein $R_1$ is methyl or ethyl.

10. A compound according to claim 1 wherein each of $R_1$ and $R_2$ is lower alkyl of 1 to 4 carbon atoms.

11. A compound according to claim 10 wherein X is naphthyl.

12. A compound according to claim 10 wherein each of $R_3$, $R_4$ and $R_5$, independently of the others, is selected from the group consisting of hydrogen, bromo, chloro, fluoro, methyl, ethyl, methoxy, acetamido and benzyloxy.

13. A compound according to claim 10 wherein each of $R_1$ and $R_2$, independently of the other, is methyl or ethyl.

14. A compound according to claim 1 which is 1-carbamyl-4-(3-phenoxy-2-hydroxypropyl)piperazine.

15. A compound according to claim 1 which is 1-carbamyl-4-[3-(4-chlorophenoxy)-2-hydroxypropyl]piperazine.

16. A compound according to claim 1 which is 1-carbamyl-4-[3-(3-bromophenoxy)-2-hydroxypropyl]piperazine.

17. A compound according to claim 1 which is 1-carbamyl-4-[3-(2-fluorophenoxy)-2-hydroxypropyl]piperazine.

18. A compound according to claim 1 which is 1-carbamyl-4-[3-(4-methylphenoxy)-2-hydroxypropyl]piperazine.

19. A compound according to claim 1 which is 1-carbamyl-4-[3-(2-methylphenoxy)-2-hydroxypropyl]piperazine.

20. A compound according to claim 1 which is 1-carbamyl-4-[3-(3-ethylphenoxy)-2-hydroxypropyl]piperazine.

21. A compound according to claim 1 which is 1-carbamyl-4-[3-(4-t-butylphenoxy)-2-hydroxypropyl]piperazine.

22. A compound according to claim 1 which is 1-carbamyl-4-[3-(4-methoxyphenoxy)-2-hydroxypropyl]piperazine.

23. A compound according to claim 1 which is 1-carbamyl-4-[3-(3-methoxyphenoxy)-2-hydroxypropyl]piperazine.

24. A compound according to claim 1 which is 1-carbamyl-4-[3-(2-methoxyphenoxy)-2-hydroxypropyl]piperazine.

25. A compound according to claim 1 which is 1-carbamyl-4-[3-(4-hydroxyphenoxy)-2-hydroxypropyl]piperazine.

26. A compound according to claim 1 which is 1-carbamyl-4-[3-(4-benzyloxyphenoxy)-2-hydroxypropyl]piperazine.

27. A compound according to claim 1 which is 1-carbamyl-4-[3-(4-acetamidophenoxy)-2-hydroxypropyl]piperazine.

28. A compound according to claim 1 which is 1-carbamyl-4-[3-(3,4-dimethoxyphenoxy)-2-hydroxypropyl]piperazine.

29. A compound according to claim 1 which is 1-carbamyl-4-[3-(2,5-dimethoxyphenoxy)-2-hydroxypropyl]piperazine.

30. A compound according to claim 1 which is 1-carbamyl-4-[3-(2,3-dimethoxyphenoxy)-2-hydroxypropyl]piperazine.

31. A compound according to claim 1 which is 1-carbamyl-4-[3-(2,3,4-trimethoxyphenoxy)-2-hydroxypropyl]piperazine.

32. A compound according to claim 1 which is 1-carbamyl-4-[3-(3-methyl-4-chlorophenoxy)-2-hydroxypropyl]piperazine.

33. A compound according to claim 1 which is 1-carbamyl-4-[3-(2-chloro-4-methoxyphenoxy)-2-hydroxypropyl]piperazine.

34. A compound according to claim 1 which is 1-carbamyl-4-[3-(2,4-dichlorophenoxy)-2-hydroxypropyl]piperazine.

35. A compound according to claim 1 which is 1-carbamyl-4-[3-(naphth-1-yloxy)-2-hydroxypropyl]piperazine.

36. A compound according to claim 1 which is 1-carbamyl-4-[3-(naphth-2-yloxy)-2-hydroxypropyl]piperazine.

37. A compound according to claim 1 which is 1-(N-methylcarbamyl)-4-(3-phenoxy-2-hydroxypropyl)piperazine.

38. A compound according to claim 1 which is 1-(N-ethylcarbamyl)-4-(3-phenoxy-2-hydroxypropyl)piperazine.

39. A compound according to claim 1 which is 1-(N,N-dimethylcarbamyl)-4-(3-phenoxy-2-hydroxypropyl)piperazine.

40. A compound according to claim 1 which is 1-(N,N-diethylcarbamyl)-4-(3-phenoxy-2-hydroxypropyl)piperazine.

41. A compound according to claim 1 which is 1-(N-methylcarbamyl)-4-[3-(naphth-1-yloxy)-2-hydroxypropyl]piperazine.

42. A compound according to claim 1 which is 1-(N-ethylcarbamyl)-4-[3-(naphth-1-yloxy)-2-hydroxypropyl]piperazine.

43. A compound according to claim 1 which is 1-(N,N-dimethylcarbamyl)-4-[3-naphth-1-yloxy)-2-hydroxypropyl]piperazine.

44. A compound according to claim 1 which is 1-(N,N-diethylcarbamyl)-4-[3-(naphth-1-yloxy)-2-hydroxypropyl]piperazine.

45. The method of effecting $\beta$-adrenergic blocking activity in humans and other animals which comprises administering thereto an effective amount of a compound according to claim 1.

46. A pharmaceutical composition comprising an amount of a compound according to claim 1 sufficient to effect a $\beta$-adrenergic blocking response in combination with a pharmaceutically acceptable carrier.

* * * * *